United States Patent
Müller et al.

(12)

(10) Patent No.: US 6,288,040 B1
(45) Date of Patent: Sep. 11, 2001

(54) MEDICAMENT EXCIPIENT PARTICLES FOR TISSUE-SPECIFIC APPLICATION OF A MEDICAMENT

(75) Inventors: Ranier H. Müller; Martin Lück, both of Berlin; Jörg Kreuter, Bad Homburg, all of (DE)

(73) Assignee: DSS Drug Delivery Service Gesellschaft zur Forderung der Foshung In Phamazeutischer Technologi und Biopharmazie mbH, Kronshagen (DE)

( * ) Notice: Subject to any disclaimer, the term of this patent is extended or adjusted under 35 U.S.C. 154(b) by 0 days.

(21) Appl. No.: 09/529,600

(22) PCT Filed: Oct. 13, 1998

(86) PCT No.: PCT/EP98/06429
§ 371 Date: Jun. 21, 2000
§ 102(e) Date: Jun. 21, 2000

(87) PCT Pub. No.: WO99/20256
PCT Pub. Date: Apr. 29, 1999

(30) Foreign Application Priority Data

Oct. 17, 1997 (DE) .............................. 197 45 950

(51) Int. Cl.[7] .......................... A61K 38/00; A61K 39/00; C07K 5/00; C07K 7/00

(52) U.S. Cl. ................................ 514/21; 514/2; 514/12; 530/300; 530/324; 530/350; 530/380; 424/184.1; 424/400; 424/489; 424/491

(58) Field of Search ................................ 514/2, 21, 12; 530/300, 324, 350, 380; 424/400, 489, 491, 184.1, 185.1

(56) References Cited

PUBLICATIONS

Blunk et al, *Eur. J. Pharm. Biopharm.*, vol. 42, No. 4, pp. 262–268, 1996.*
Müller et al, Scientific and Clinical Applications of Magnetic Carriers, edited by Häfeli et al., Plenum Press, New York, pp. 135–148, 1997.*
Lück et al., *Journal of Controlled Release*, vol. 55, pp. 107–120, 1998.*

* cited by examiner

*Primary Examiner*—Avis M. Davenport
(74) *Attorney, Agent, or Firm*—Jeffrey S. Melcher; Manelli Denison & Selter, PLLC

(57) ABSTRACT

The invention relates to medicament excipient particles which are suitable for tissue-specific application of a medicament, especially to the central nervous system (CNS). The invention particles can be loaded with or be free pf the active substance. At least one detection protein is bonded to the particle surface or alternatively, the particle surface is modified in such a way that a detection protein bonds with it on contact.

55 Claims, 4 Drawing Sheets

MEDICAMENT EXCIPIENT PARTICLES FOR TISSUE-SPECIFIC APPLICATION OF A MEDICAMENT

Figure 1:
Figure 1:
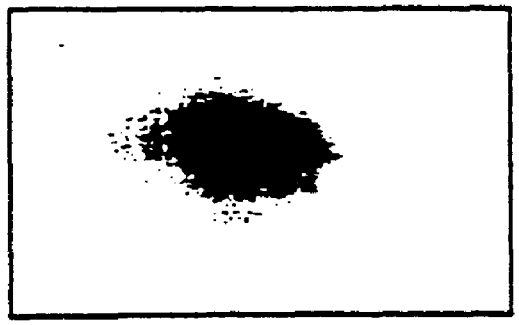

This application is a 371 of PCT/EP98/06429 filed Oct. 13, 1998.

The invention relates to drug carrier particles which are suitable for site-specific drug application, especially to the central nervous system (CNS).

The treatment of CNS diseases is made difficult by the blood-brain barrier, one of the most important and most impermeable physiological barriers in the body. The vascular endothelium of the brain capillaries is regarded primarily as a morphological substrate of the blood-brain barrier as the intercellular gaps between the endothelial cells are bridged by tight cell-cell-connections ("tight junctions"). The endothelial cells are surrounded moreover by an unbroken basal membrane. The lack of fenestration, the absence of pores and a low pinocytotic activity are typical of the tissue. In addition to this, the blood vessels are enclosed in a closely adjacent layer of glial cells in the area of the CNS (Thews, G., Mutschler, E., Vaupel, P., *Anatomie, Physiologie und Pathophysiologie des Menschen*, $3^{rd}$ Edition, Wissenschaftliche Verlagsgesellschaft, Stuttgart, 1989; Borchard, G., in: Müller, R. H., Hildebrand, G. (Ed.), *Pharmazeutische Technologie: Moderne Arzneiformen*. Wissenschaftliche Verlagsgesellschaft, Stuttgart, 1997, 291–296). As a rule, therefore, the brain can be reached from the blood only by lipophilic drugs with a low molecular weight (MW<500) (Pardridge, W. M., *J. Control. Rel.*, 39, 281–286, 1996).

The blood-brain barrier is normally not permeable for very many active substances such as e.g. peptides, proteins and oligonucleotides as possible therapeutics for CNS diseases.

According to Pardridge (*J. Control. Rel.*, 39, 281–286, 1996), the strategies for a drug delivery into the brain can be divided into a) invasive b) pharmacological and c) physiological procedures.

With invasive techniques, the blood-brain barrier can be physically circumvented, e.g. by implanting a drug carrier system into the brain (Domb, A. J., Ringel, I., in: Flanagan, T. R., Emerich, D. F., Winn, S. R. (Ed.), *Providing Pharmacological Access to the Brain*. Academic Press, Inc., New York, 1994, 169–187; Friden, P. M., *J. Control. Rel.* 46, 117–128, 1996). A disadvantage of these techniques is that they involve a surgical operation and for that reason have not established themselves as a common method of treatment.

The pharmacological strategies for a drug delivery through the blood-brain barrier include measures for increasing the lipophilicity of drugs (Chekhonin, V. P., Kabanov, A. V., Zhirkov, Y. A., Morozov, G. V., *FEBS Lett.*, 287, 149–152, 1991). Disadvantages of these procedures are that "new drug entities" form, for which extensive cost-intensive toxicological studies have to be carried out, that these procedures are practicable only for relatively small molecules and that they have a low efficiency (Friden, P. M., *J. Control. Rel.*, 46, 117–128, 1996; Pardridge, W. M., *J. Control. Rel.*, 39, 281–286, 1996).

Physiological strategies for a drug delivery into the brain are based on the knowledge of special active specific delivery mechanisms to the blood-brain barrier e.g. for nutrients (amongst other glucose and amino acids), peptides or proteins (Pardridge, W. M., *Peptide Drug Delivery to the Brain*, Raven Press, New York, 1991; Pardridge, W. M., *J. Control. Rel.*, 39, 281–286, 1996; Friden, P. M., *J Control. Rel.*, 46, 117–128, 1996). An example is L-dopa as pro-drug of the neurotransmitter dopamine which the blood-brain barrier is not able to overcome. On the other hand, L-dopa is transported through the blood-brain barrier into the brain cells by an active transport mechanism for neutral amino acids ("neutral amino acid carriers"), where the actual active form dopamine is formed (Mutschler, E., *Arzneimittelwirkungen, Lehrbuch der Pharmakologie und Toxikologie*, $7^{th}$ Edition, Wissenschaftliche Verlagsgesellschaft, Stuttgart, 1996; Borchard, G., in: Müller, R. H., Hildebrand, G. (Ed.), *Pharmazeutische Technologie: Moderne Arzneiformen*, Wissenschaftliche Verlagsgesellschaft, Stuttgart, 1997, 291–296). But this approach has not been widely implemented either, due to the following disadvantages:

1. the active transport mechanisms are very substrate-specific, i.e. only a few drugs very similar to the substrate are delivered, which greatly limits the usability of this strategy.

2. conjugates of natural substrate and drug are not, or not very efficiently, delivered because of the pronounced specificity of the transport system (chemical structure and three-dimensional structure and size of the substrate to be delivered).

Another approach to site-specific drug administration, e.g. into the CNS, is the incorporation of drugs into particulate drug carriers such as nanoparticles, microparticles, emulsions and liposomes as well as processing into particulate forms of drugs such as hydrosols, nanocrystals and nanosuspensions. For intravenously injected particles the crossing of the endothelia is generally even more difficult, due to their size (as a rule>>30 nm), than for drug molecules (size in the Angström range). Thus for example a very limited ability to penetrate through the blood-brain barrier is generally described for liposomes (Gennuso, R., Spigelman, M. K., Chinol, M., Zappulla, R. A., Nieves, J., Vallabhajosula, S., Paciucci, P. A., Goldsmith, S. J., Holland, J. F., *Cancer Invest.*, 11, 118–128, 1993; Boado, R. J., *Adv. Drug Deliv. Rev.*, 15, 73–107, 1995; Boado, R. J., *Proceed. Intern. Symp. Control. Rel. Bioact. Mater.*, 24, 223–224, 1997; Pardridge, W. M., *J. Control. Rel.*, 39, 281–286, 1996).

Alyautdin et al. (Alyautdin, R. N., Gothier, D., Petrov, V. E., Kharkevich, D. A., Kreuter, J., *Eur. J. Pharm. Biopharm.*, 41, 44–48, 1995) published a first success as regards the application of a drug to the CNS with particulate carriers. They demonstrated, for i.v. administered polybutylcyanoacrylate (PBCA) nanoparticles, to the surface of which the analgesically effective substance dalargin was bound by adsorption, a dose-dependent analgesic effect in the "tail-flick-test" on mice. The hexapeptide dalargin (Tyr-D-Ala-Gly-Phe-Leu-Arg) is a leu-enkephalin-analogon and has a centrally analgesic effect as opioid receptor agonist. Dalargin cannot normally overcome the blood-brain barrier.

An i.v. administration of dalargin does not lead to an analgesic effect in spite of the stability in the blood even in high dosage (20 mg/kg) (Kalenikova E. I., Dmitrieva, O. F., Korobov, N. N., Zhukova, S. V., Tischenko, V. A., *Vopr. Med. Khim.*, 34, 75–83, 1988).

In another study, an accumulation of the particles in the area of the brain was detected in the rat model after intravenous injection of surface-modified polymethyl methacrylate (PMMA) nanoparticles (Tröster, S. D., Müller, U., Kreuter, J., *Int. J. Pharm.*, 61, 85–100, 1990). But the authors ruled out the possibility that the particles are absorbed in brain cells, which rules out a drug administration into the brain.

It is disadvantageous that the phenomenon reported by Alyautdin et al. (*Eur. J. Pharm. Biopharm.*, 41, 44–48, 1995)

and by Schröder and Sabel (*Brain Res.*, 710, 121–124, 1996) cannot be used for a targeted and controlled drug administration. The mechanism is not known. There remains only the "trial and error procedure" to detect whether an addition of a surfactant to a particulate carrier perhaps produces by chance an accumulation in the brain. The probability that this happens is low, as surfactants were often used in particle preparations (Couvreur, P., Dubernet, C., Puisieux, F., *Eur. J. Pharm. Biopharm.*, 41, 2–13, 1995) and up until now the above reports are the first data concerning an absorption of a drug in the brain.

For drug delivery specifically into the desired target tissue, in particular also into the brain, a form of drug would be optimal which 1. combines the specificity of a transport route for example via receptor-mediated transcytosis (physiological strategy) with the high delivery capacity of particulate drug carriers, e.g. liposomes, emulsions or nanoparticles,
2. facilitates the absorption of the drug into the tissue— e.g. the brain—via a generally usable recognition molecule and
3. allows a controlled attachment of the recognition molecule to the surface of particles.

The advantage of particulate drug carriers—in contrast to e.g. molecule conjugates—is, besides the high delivery capacity, the possibility of delivering many drugs which differ in their physiochemical properties and their molecular weight via the choice of carrier-matrix (e.g. polymer, lipid, phospholipid) and manufacturing conditions of the particles (Borchard, G., in: Müller, R. H., Hildebrand, G. (Ed.), *Pharmazeutische Technologie: Moderne Arzneiformen*. Wissenschaftliche Verlagsgesellschaft, Stuttgart, 1997, 291–296).

The object of the invention is therefore to create drug carrier particles which are able to overcome the blood-brain barrier and introduce desired active drug substances into the CNS.

This object is achieved according to claim 1 by drug carrier particles, in active substance-loaded or active substance-free form, where at least one recognition protein, or at least the part of it recognising the receptor, is bound to the particle surface.

Preferred versions are subjects of the dependent claims.

Polymers, the drug itself (nanosuspensions, hydrosols), solid lipids, liquid lipids, o/w emulsions, w/o/w emulsions or phospholipid vesicles are suitable in particular as particle material.

Drug carrier particles which are modified by binding a recognition protein (also proteins occurring naturally in the blood) to the particle surface, preferably apolipoprotein E, or by binding several recognition proteins, can deliver drugs specifically to the target tissue, in particular to the central nervous system (CNS). The recognition proteins are adsorbed onto the particle surface, covalently bound to it or preferentially adsorbed by controlled modification of the particle surface (chemical, physical, adsorption of molecules mediating the adsorption of the recognition protein).

The adsorption of the recognition proteins can take place before administration of the drug carriers or also—after suitable modification of the surface of the drug carriers—in vivo in the body. Physiological recognition proteins present in the body, in particular apolipoprotein E, preferentially adsorb on administered drug carriers, in particular on carriers modified with special surfactants or polymers, which for example may have been introduced into the body by intravenous administration.

The recognition protein can be bound to the surface of the particles by non-specific or specific adsorption.

Furthermore, the recognition protein can be covalently bound to the surface of the particles. To this end, a binding is preferably effected to particles with reactive surface groups, in particular epoxy or aldehyde groups, or after activation of the particle surface with activators, in particular carbodiimide, N-ethoxycarbonyl-2-ethoxy-1,2-dihydroquinoline, glutardialdehyde, bromzyane, metaperiodate (Na-salt or K-salt), tosyl chloride and chloroformic acid ester. The binding of the recognition proteins can be performed via their amino groups.

In addition, the recognition protein can be bound to the surface of the particles by preferential adsorption. The preferential adsorption can take place from protein solutions or by contact of the particles with plasma, serum or blood, the latter also being able to take place ex vivo or in vivo.

The surface of the particles can preferably be chemically modified before the preferential adsorption by introducing functional groups, in particular hydroxyl, carboxyl, amino, hydroxyethyl, epoxy or aldehyde groups and their derivatives or the surface properties changed by physical treatment with plasma, in particular plasma etching, in order to introduce hydroxyl groups.

Furthermore, the surface can be modified by adsorption of substances which lead to a preferential adsorption of the recognition protein, the modifying substance being used in relation to the drug particle in a weight-related amount of 0.01 to 10 parts modifying substance per 1 part particle, preferably 0.1 to 10 parts modifying substance per 1 part particle, and in particular 1 part modifying substance per 1 part particle.

Suitable substances include in particular surfactants, specially ethoxylated surfactants, preferably polyethylene glycol fatty acid esters and polyethylene glycol fatty alcohol ethers, preferably polyethylene glycol sorbitan fatty acid esters and polyethylene glycol fatty acid glycerides, preferably Tween® 20, 40, 60 and 80 or Cremphor® El and RH40.

Polymers, in particular polymers from the poloxamers and poloxamines, celluloses and their derivatives, preferably methylcellulose, hydroxyethylcellulose, hydroxypropylmethylcellulose, hydroxypropylcellulose, carboxymethylcellulose sodium as well as xanthan, polyvinyl alcohol, polyvinylpyrrolidone, polyacrylic acids, polyethylene glycols, polyethylene glycol-containing block copolymers, starch and derivatives, dextran and derivatives, polyethyleneimine and gelatins are for example suitable.

The recognition protein is preferably a recognition protein occurring naturally in the blood. Preferred recognition proteins are apolipoprotein E, apolipoprotein A-I, A-II, A-IV, B, C-II, C-III, D, H and/or J. The recognition protein is preferably apolipoprotein E, which can be present in combination with one or several other recognition proteins, in particular with apolipoprotein A-I, A-II, A-IV, B, C-II, C-III, D H and/or J, and/or with albumin.

Apo C-II, apo C-III, apo A-IV, apo-E are preferably used individually or in combinations of 2 or 3 or 4 apolipoproteins.

The recognition protein is generally used, in relation to the drug carrier, in an amount of 0.001 to 40 wt. %, in particular 0.01 to 30 wt. % and preferably 0.1 to 15 wt. %.

Various receptors exist for apolipoprotein (apo) E which belong to the family of the LDL receptors (Schneider, W. J., Nimpf, J., *Curr. Opin. Lipid.*, 4, 205–209, 1993).

ApoE receptors are also located at the blood-brain barrier. In the liquor cerebrospinalis, the absorption of lipoproteins via cellular LDL receptors is mediated exclusively by ApoE according to knowledge to date. ApoE is predominantly synthesized and separated in the astrocytes. These cells also express LDL receptors (Boyles, J. K., Pitas, R. E., Wilson, E., Mahley, R. W., Taylor, J. M., *J. Clin. Invest.*, 76, 1501–1513, 1985; Weisgraber, K. H., Roses, A. D., Strittmatter, J., *Curr. Opin. Lipid.*, 5, 110–116, 1994).

In summary, it can be ascertained that various receptor systems exist in the areas of the brain and the blood-brain barrier, which could facilitate a delivery of ApoE or ApoE-containing particles into the brain.

In order to demonstrate the role of the protein, it had to be shown that an accumulation of a particle takes place in a tissue after binding of the apolipoprotein E, regarded as responsible for the accumulation, to the surface of the particle was carried out.

To demonstrate the function of ApoE, particles were used on the surface of which ApoE from plasma does not adsorb.

Unmodified polybutylcyanoacrylate (PBCA) particles from example 1 were therefore used, for which the absence of ApoE on the surface was demonstrated after incubation with plasma. Incubation of the particles with a solution of ApoE led to an adsorption on the surface (example 2). It is thus possible to bind ApoE to the surfaces of particulate carriers by a simple adsorption process.

Surprisingly, ApoE has thus been Identified as a Protein which Simultaneously a) was present in a relatively large amount on tissue-specific particles b) in the presence of which a CNS effectiveness took place (example 1), c) in the absence of which a CNS effectiveness was absent (example 4)

d) and with which, on the basis of the receptors described in the literature, a recognition and mediation effect is also theoretically possible.

The correct conformation of the adsorbed recognition protein (molecule segment binding to the receptor exposed in a molecular conformation that is able to bind to the receptor) is of essential importance for the delivery to the target tissue, here the CNS. From the point of view of drug approval and registration (avoidance of a "new entity"), the recognition protein should—if possible—not be covalently bound to the particles, as this makes a toxicity study necessary for every form of drug during approval. Binding to the surface by adsorption is technologically easier.

There are problems:

1. Does the ApoE also adsorb at the particle surface without the presence of a surfactant such as e.g. Tween® 80, which leads to an automatic accumulation of ApoE?

2. Does ApoE remain, when binding by adsorption, after intravenous injections on the particle surface?

3. Is ApoE adsorbed in the correct conformation so that it can bind to the target tissue and mediates a CNS effectiveness?

In particular, the possible desorption or displacement of ApoE from the surface (see 2.) and the need for the correct conformation of the adsorbed ApoE (see 3.) made it appear highly unlikely that a drug delivery to the brain would take place.

Pre-adsorbed ApoE could possibly be displaced from the particle surface by other plasma proteins after an intravenous administration. In order to simulate and analyse this possible displacement process the plasma protein adsorption pattern were determined of PBCA particles, to the surface of which ApoE had been previously bound by adsorption. Pre-adsorbed ApoE was retained on the surface even after subsequent incubation in plasma (example 3).

The observed analgesic effect results from a receptor-mediated process at the blood-brain barrier. For this reason, adsorbed ApoE must be present on the surface in a conformation which allows a binding to an ApoE receptor. This applies to pre-adsorbed or covalently bound ApoE as well as to ApoE molecules which reach the surface of the particles by adsorption from plasma.

Surfactant-free PBCA particles with pre-adsorbed ApoE were examined in the "tail-flick-test" on mice with regard to their potential to deliver dalargin through the blood-brain barrier and to achieve an analgesic effect. Unmodified PBCA particles were unable to overcome the blood-brain barrier after i.v. application (Alyautdin, R. N., Gothier, D., Petrov, V. E., Kharkevich, D. A., Kreuter, J., *Eur. J. Pharm. Biopharm*., 41, 44–48, 1995: Kreuter, J., Alyautdin, R. A., Kharkevich, D. A., Ivanov, A., *Brain Res*., 674, 171–174, 1995; Schröder, U., Sabel, B. A., *Brain Res*., 710, 121–124, 1996; Alyautdin, R. N., Petrov, V. E., Langer, K., Berthold, A., Kharkevich, D. A., Kreuter, J., *Pharm. Res*., 14, 325–328, 1997). The i.v. application of the PBCA nanoparticles with pre-adsorbed ApoE led however to an analgesic effect. 15 minutes after the injection of the particles an effect was observed which accounted for 44% of the maximum possible effect (example 1). Contrary to expectations, ApoE adsorbed in the correct conformation and remained adsorbed, even after i.v. injection, in sufficiently stable manner to deliver dalargin into the CNS.

The fact that unmodified particles to which ApoE was bound before the i.v. application produce an analgesic effect proves the participation of ApoE in the increased delivery of the dalargin-charged PBCA particles through the blood-brain barrier.

A model is described for ApoE according to which the protein consists of two structurally different domains (Weisgraber, K. H., *Adv. Prot. Chem*., 45, 249–303, 1994; Weisgraber, K. H., Roses, A. D., Strittmatter, J., *Curr. Opin. Lipid*., 5, 110–116, 1994). According to this, ApoE has an amino-terminal globular (i.e. structurally stable) domain and a carboxy-terminal more labile domain, which inclines more strongly to the unfolding of its structure. The N-terminal domains contain the part of the protein which interacts with potential receptors, the C-terminal domain being responsible for the binding to lipids (e.g. in HDL) (Weisgraber, K. H., *Adv. Prot. Chem*., 45, 249–303, 1994). Surprisingly, the affinity of this C-terminal domain to surfaces was sufficient for a) a sufficient binding of ApoE to the particle surface to took place, b) the adsorption to be sufficiently stable to also keep ApoE present on the surface during contact with plasma proteins, c) the C-terminal domain and not the n-terminal domain to bind on the surface band and d) the structure of the more stable N-terminal domain and thus the affinity to potential receptors to be retained.

Surprisingly, ApoE has thus been Identified as a Protein which Simultaneously adsorbs onto the surface of a particle, remains stably bound to the surface and is not completely displaced by other plasma proteins (e.g. after intravenous injection) and adsorbs in the correct conformation so that it can bind to the target tissue (in this case blood-brain barrier and CNS) and mediates a CNS effectiveness of the drug.

The recognition protein(s) can be adsorbed onto the surface of unmodified particles (Example 2, PBCA particles) or alternatively after previous modification of the surface (Example 2, PBCA particles modified by adsorbed surfactant). For the tissue-specific accumulation in the brain, surfactants have to be selectively chosen for this which for example enrich ApoE at the surface (e.g. Tween, Example 2), so that a CNS effect takes place in vivo (Table 1). Surfactants which do not have this effect, such as poloxamer 407 (Example 4) produce no drug effect in the CNS in vivo (Table 1) either.

The adsorption of the recognition proteins can take place ex vivo (e.g. from ApoE solution, plasma, serum, blood), in order to produce a CNS effect in vivo (Example 1).

After controlled modification of the particle surface to achieve the preferential adsorption of ApoE, this can however also take place in vivo after contact with blood (Table 1).

For drug carriers with a very hydrophilic surface it may be that the affinity of the recognition protein is not sufficient to adsorb at the surface to a sufficient extent. It is just as possible that the molecule segment needed to bind to the receptor adsorbs (in the case of ApoE e.g. the N-terminal domain). In this case, the recognition protein can be covalently bound to functional groups of the surface, the binding to the surface taking place via molecule segments which are not needed for the binding to the receptor of the target tissue (in the case of ApoE e.g. the C-terminal domain). Examples 5 and 6 show the covalent binding of a recognition protein to the surface of a polymer nanoparticle. As an alternative to the binding-on of the whole recognition protein, parts of the molecule can also be used which contain the molecule part binding to the receptor.

In the following table, examples are listed of relevant activation and coupling reagents for a chemico-covalent coupling of the protein to the carrier matrix.

The following substances are used for the chemical activation, as a precursor of a covalent coupling of functional groups of a biomolecule with those on a solid carrier.

| Particle | biomolecule | substance |
|---|---|---|
| —COOH | —NH$_2$ | carbodiimide (water-soluble) (1-ethyl-3-(3-dimethylaminopropyl)-carbodiimide-hydrochloride) |
| —COOH | —NH$_2$ | EEDQ (N-ethoxycarbonyl-2-ethoxy-1,2-dihydroquinoline) |
| —NH$_2$ | —NH$_2$ | glutardialdehyde |
| —OH (in aq.) | —NH$_2$ | bromzyane (BrOCN) |
| —CH$_2$—CH$_2$—OH | —NH$_2$ | meta-periodate (Na/K) JO$_3$ |
| —OH (in org.LM) | —NH$_2$ | tosyl chloride |
| —OH (in org.LM) | —NH$_2$ | chloroformic acid ester |

So-called "ready to use" particles with reactive surface groups require no chemical activation as coupling precursor:

| —CH(O)—CH2 Epoxy- | —NH$_2$ —OH —COOH | — |
|---|---|---|
| —CHO aldehyde | —NH$_2$ | — |

In general, the carriers can contain the following chemical active substance groups:
hydroxylated hydrocarbons
carbonyl compounds such as ketones (e.g. haloperidol), monosaccharides, disaccharides and amino sugars
carboxylic acids such as aliphatic carboxylic acids, esters of aliphatic and aromatic carboxylic acids, basically substituted esters of aliphatic and aromatic carboxylic acids (e.g. atropine, scopolamine), lactones (e.g. erythromycin), amides and imides of aliphatic carboxylic acids, amino acids, aliphatic aminocarboxylic acids, peptides (e.g. ciclosporin), polypeptides, β-lactam derivatives, penicillins, cephalosporins, aromatic carboxylic acids (e.g. acetylsalicylic acid), amides of aromatic carboxylic acids, vinylogous carboxylic acids and vinylogous carboxylic acid esters carbon dioxide derivatives such as urethane and thiourethanes, urea and urea derivatives, guanidine derivatives, hydantoins, barbituric acid derivatives and thiobarbituric acid derivatives nitro compounds such as aromatic nitro compounds and heteroaromatic nitro compounds amines such as aliphatic amines, aminoglycosides, phenylalkyl amines, ephedrine derivatives, hydroxyphenylethanolamines, adrenaline derivatives, amphetamine derivatives, aromatic amines and derivatives, quaternary ammonium compounds sulfurous compounds such as thiols and disulphanes sulphones, sulphonic acid esters and sulphonic acid amides polycarbocycles such as tetracyclines, steroids with aromatic ring A, steroids with an alpha, beta-unsaturated carbonyl function in ring A and alpha ketol group (or methylketo group) at C-17, steroids with a butenolide ring at C-17, steroids with a pentadienolide ring at C-17 and seco-steroids O-containing heterocycles such as chromane derivatives (e.g. cromoglycic acid)

N-containing heterocycles such as pyrazole derivatives (e.g. propyphenazone, phenylbutazone)

imidazole derivatives (e.g. histamine, pilocarpine), pyridine derivatives (e.g. pyridoxine, nicotinic acid), pyrimidine derivatives (e.g. trimethoprim), indole derivatives (e.g. indomethacin), lysergic acid derivatives (e.g. ergotamine), yohimbime derivatives, pyrrolidine derivatives, purine derivatives (e.g. allopurinol), xanthine derivatives, 8-hydroxyquin oline derivatives, amino-hydroxy-alkylated quinolines, aminoquinolines, isoquinoline derivatives (e.g. morphine, codeine), quinazoline derivatives, benzopyridazine derivatives, pteridine derivatives (e.g. methotrexate), 1,4-benzodiazepine derivatives, tricyclic N-containing heterocycles, acridine derivatives (e.g. ethacridine) and dibenzazepine derivatives (e.g. tirmipramine)

S-containing heterocycles such as thioxanthene derivatives (e.g. chlorprothixene)

N,O- and N,S-containing heterocycles such as monocyclic N,O-containing heterocycles, monocyclic N,S-containing heterocycles, thiadiazine derivatives, bicyclic N,S-containing heterocycles, benzothiadiazine derivatives, tricyclic N,S-containing heterocycles and phenothiazine derivatives O,P,N-containing heterocycles (e.g. cyclophosphamide).

Examples of drug groups and drugs to be specially in corporated into the carriers (as salt, ester, ether or in free form) are:

Analgesics/antirheumatics

BTM bases such as morphine, codeine, heroin, piritamide, diamorphine, dihydrocodeine, hydromorphone, hydrocodone, pethidine, fenpipramide, piritramide, clofedanol, pentazocine, buprenorphine, nalbuphine, tilidine, fentanyl and fentanyl derivatives, levomethadone, tramadol, diclofenac, ibuprofen, indomethacin, naproxen, piroxicam, penicillamine, ademetionine, flupirtine, acetylsalicylic acid Antiallergics pheniramine, dimethindene, terfenadine, astemizole, loratidine, doxylamine, meclozine, bamipine, clemastine Anti-asthmatics terbutaline, beclomethasone, cromoglycic acid, reproterol, salbutamol, nedocromil Antibiotics/chemotherapeutics of these: rifampicin, amoxicillin, azlocillin, bacampicillin, benzylpenicillin, amikacin, azithromycin, ciprofloxacin, norfloxacin, polypeptide antibiotics such as colistin, polymyxin B, teicoplanin, vancomycin; antimalarials such as quinine, halofantrine, chloroquine, virustatics such as ganciclovir, foscarnet, zidovudine, acyclovir and others such as brivudine, dapsone, fosfomycin, fusafungine, trimethoprim, amphotericin Antidotes mesna Antiemetics tropisetron, scopolamine, thiethylperazine Antiepileptics phenytoin, mesuximide, ethosuximide, primidone, phenobarbital, valproic acid, carbamazepine, clonazepam, diazepam, nitrazepam, vigabatrine, lamotrigine, trimethadione, sulthiame Antifibrinolytics aminomethylbenzoic acid Antihypertonics/beta-receptor blockers/calcium-antagonists/ACE-inhibitors bupranolol, captopril, fosinopril, sodium nitroprusside, isradipine, mepindolol Antihypotonics cafedrine, dihydroergotamine Anticoagulants heparin, certoparin Antimycotics nystatin, natamycin, amphotericin B, flucytosine, miconazole, fluconazole, itraconazole, clotrimazole, econazole, tioconazole, fenticonazole, bifonazole, oxiconazole, ketoconazole, isoconazole, tolnaftate, amorolfine, terbinafine Corticoids aldosterone, fludrocortisone, betametasone, dexametasone, triamcinolone, fluocortolone, hydroxycortisone, prednisolone, prednylidene, cloprednol, methylpredinsolone Diagnostics a) radioactive isotopes such as Te99m, In111 or I131, covalently bound to lipids or lipoids or other molecules or in complexes b) highly-substituted iodine-containing compounds such as e.g. lipids c) meglumine amidotrizoate, iotroxic acid, sodium ipodate Diuretics hydrochlorothiazide Erythropoietin Fibrinolytics urokinase Haemostiptics/anti-hemorrhagics blood-coagulation factors VIII, IX Hypnotics, sedatives cyclobarbital, pentobarbital, phenobarbital, methaqualone (BTM), benzodiazepines (flurazepam, midazolam, nitrazepam, lormetazepam, flunitrazepam, triazolam, brotizolam, temazepam, loprazolam), thalidomide, zolpidem, zopiclone, diphenhydramine, doxylamine, temazepam Hypophysial, hypothalamic hormones, regulatory peptides and their inhibitors corticotrophin, tetracosactide, choriogonadotropin, urofollitropin, urogonadotropin, somatropin, metergoline, bromocriptine, terlipressin, desmopressin, oxytocin, argipressin, ornipressin, leuprorelin, triptorelin, gonadorelin, buserelin, nafarelin, goselerin, somatostatin, quinagolide, octreotide acetate, lypressin Immunotherapeutics and cytokines dimepranol-4-acetatamidobenzoate, thymopentin, a-interferon, β-interferon, g-interferon, filgrastim, interleukins, azathioprine, ciclosporin, molgramostim, GM-CSF Coronary agents glycerol trinitrate, isosorbide dinitrate, oxyfedrine Liver therapeutics sylimarin Antihyperlipoproteinemics pravastatin, fluvastatin Local anaesthetics butanilicaine, mepivacaine, bupivacaine, etidocaine, lidocaine, articaine, prilocaine, propipocaine, oxybuprocaine, tetracaine, benzocaine Anti-migraine agents proxibarbal, lisuride, methysergide, dihydroergotamine, clonidine, ergotamin, pizotifen, sumatriptan Muscle relaxants tubocurarine, alcuronium, pancuronium, vecuronium, atracurium, suxamethonium, dantrolene, baclofen, carisoprodol, chlormezanone, memantine, tizanidine Narcotics methohexital, propofol, etomidate, ketamine, alfentanil, thiopental, droperidol, fentanyl, alfentanil, sufentanil Parathyroid gland hormones, calcium metabolism regulators dihydrotachysterol, calcitonin, clodronic acid, etidronic acid, pamidronic acid Neuropathological preparations α-lipoic acid Prostaglandins alprostadil Psychopharmacological agents benzodiazepins (lorazepam, diazepam), clomethiazole, Thyroid treatments 1-thyroxine, carbimazole, thiamazole, propylthiouracil Sera, immunoglobulins, vaccines a) immunoglobulins generally and specifically such as hepatitis types, rubella, cytomegalia, rabies, FSME, varicella-zoster, tetanus, Rhesus factors b) immune sera such as botulism-antitoxin, diphtheria, gas gangrene, snake venom, scorpion poison c) vaccines such as influenza, tuberculosis, cholera, diphtheria, hepatitis types, FSME, rubella, haemophilus influenzae, measles, neisseria, mumps, poliomyelitis, tetanus, rabies, typhus Sexual hormones and their inhibitors
anabolics, androgens, antiandrogens, gestagens, oestrogens, antioestrogens (tamoxifen, etc.), flutamide, fosfestrol, cyproterone, formestane, aminoglutethimide Toxoplasmosis agents
atovaquone Urologics
trospium chloride Vitamins
Alfacalcidol, vitamin A and derivatives, vitamin E and derivatives, ascorbic acid CNS treatments
a) neuroleptics such as perazine, promazine, sulpiride, thioridazine, chlorprothixene, levomepromazine, prothipendyl, chlorpromazine, clopenthixol, triflupromazine, perhpenazine, trifluperazine, pimozide, reserpine, fluphenazine, haloperidol, trifluperidol, benperidol, alimemazine, fluphenazine, flupentixol, melperone, bromperidol, pipamperone, clozapine, risperidone,
b) antidepressants such as imipramine, desipramine, trimipramine, lofepramine, clomipramine, opipramol, amitriptyline, amitriptylinoxide, nortriptyline, dibenzepin, doxepin, maprotiline, mianserin, fluoxetine, fluvoxamine, paroxetine, trazodone, moclobemide, tranylcypromine, oxitriptan, viloxazine, hypericin, lithium salts
c) tranquillizers such as meprobamate, hydroxyzine, benzodiazepines such as chlordiazepoxide, diazepam, prazepam, oxazepam, potassium-clorazepate, lorazepam, clonazepam, bromazepam, clotiazepam, alprazolam, clobazam, buspirone
d) psychostimulants such as caffeine, theophylline, theobromine, amphetamines and related substances
e) substances for treating demential syndromes such as meclofenoxate, nicergoline, piracetam, pyritinol, tacrine, memantine, dihydroergotoxine methanesulphonate
f) anorectics such as nor-pseudoephedrine, amfepramone, mefenorex, levopropylhexedrine, fenfluramine, dexfenfluramine
g) analeptics such as doxapram, fenethylline
h) nerve growth factors, naloxone, dalargine
i) antiparkinsonians such as L-dopa, selegiline, bromocriptine, amantadine, tiapride, biperiden, trihexyphenidyl, procyclidine, benzatropin, orphenadrine, bornaprine, methixene, α-dihydroergocryptine, carbidopa Cystostatics and metastasis inhibitors
a) alkylating drugs such as nimustine, melphalan, carmustine, lomustine, cyclophosphamide, ifosfamide, trofosfamide, chlorambucil, busulfan, treosulfane, prednimustine, thiotepa,
b) antimetabolites such as cytarabine, fluorouracil, methotrexate, mercaptopurine, tioguanine
c) alkaloids such as vinblastine, vincristine, vindesine
d) antibiotics such as aclarubicin, bleomycin, dactinomycin, daunorubicin, doxorubicin, epirubicin, idarubicin, mitomycin, plicamycin
e) complexes of sub-group elements (e.g. Ti, Zr, V, Nb, Ta, Mo, W, Ru, Pt) such as carboplatin, cisplatin and metallocene compounds such as titanocene dichloride
f) amsacrine, dacarbazine, estramustine, etoposide, hydroxycarbamide, mitoxanthrone, procarbazine, temiposide
g) alkylamidophospholipids (described in J. M. Zeidler, F. Emling, W. Zimmermann and Roth, H. J., Archiv der Pharmazie, 324, 687, 1991)
h) ether lipids such as hexadecylphosphocholine, ilmofosine and analogues (described in Zeisig, R., Arndt, D., Brachwitz, H., Pharmazie 45 809–818 1990)
i) taxanes such as paclitaxel and docetaxel
j) altretamine, aminoglutethimide, asparaginase, hydroxycarbamide, miltefosine

EXAMPLES

Example 1

Unmodified, dalargin-charged PBCA-nanoparticles were not able to cross the blood-brain barrier after i.v. application. The i.v. application of these nanoparticles with pre-adsorbed ApoE to mice led however to an analgesic effect in the "tail-flick-test" described by Alyautdin et al. (Alyautdin, R. N., Gothier, D., Petrov, V. E., Kharkevich, D. A., Kreuter, J., *Pharm. Biopharm.*, 41 44–48, 1995). 15 minutes after i.v. injection of the particles, an effect was observed which accounted for 44% of the maximum possible effect (calculation of the effect according to a formula given by Alyautdin et al.) (Alyautdin, R. N., Gothier, D., Petrov, V. E., Kharkevich, D. A., Kreuter, J., *Eur. J. Pharm. Biopharm.*, 41, 44–48, 1995).

Example 2

ApoE solutions (50 mg ApoE in 160 µl $NH_4HCO_3$-buffer (10 mM), pH 7.5, Calbiochem-Novabiochem, Nottingham, UK) were incubated in each case in 500 µl of a 6-percent suspension (m/V) of unmodified PBCA particles and PBCA particles modified with Twee® 80 for 3 hours at 37° C. (Tamada and Ikada, 1993). The particles were separated from the dispersion medium by centrifugation and washed four times. The adsorbed ApoE was desorbed from the particle surface with solubilising solutions described by Hochstrasser et al. (Hochstrasser, D. F., Harrington, M. G., Hochstrasser, A.-C., Miller, M. J., Merril, C. R., Anal. Biochem., 173, 424–435, 1988). 80 µl of each of the protein-containing solutions were applied to the $1^{st}$ dimension tube gels of the 2-DE. The detection of the adsorbed ApoE took place with two-dimensional electrophoresis (2-DE) according to Blunk (Blunk, T., Hochstrasser, D. F., Sanchez, J.-C., Müller, B., Müller, R. H., *Electrophoresis*, 14, 1382–1387, 1994).

FIG. 1 shows the resulting ApoE spots on the 2-DE gels of the unmodified PBCA particles and the PBCA particles modified with Tween® 80. The accumulation of ApoE is thus at its greatest on the unmodified particles.

Example 3

Figure 2:
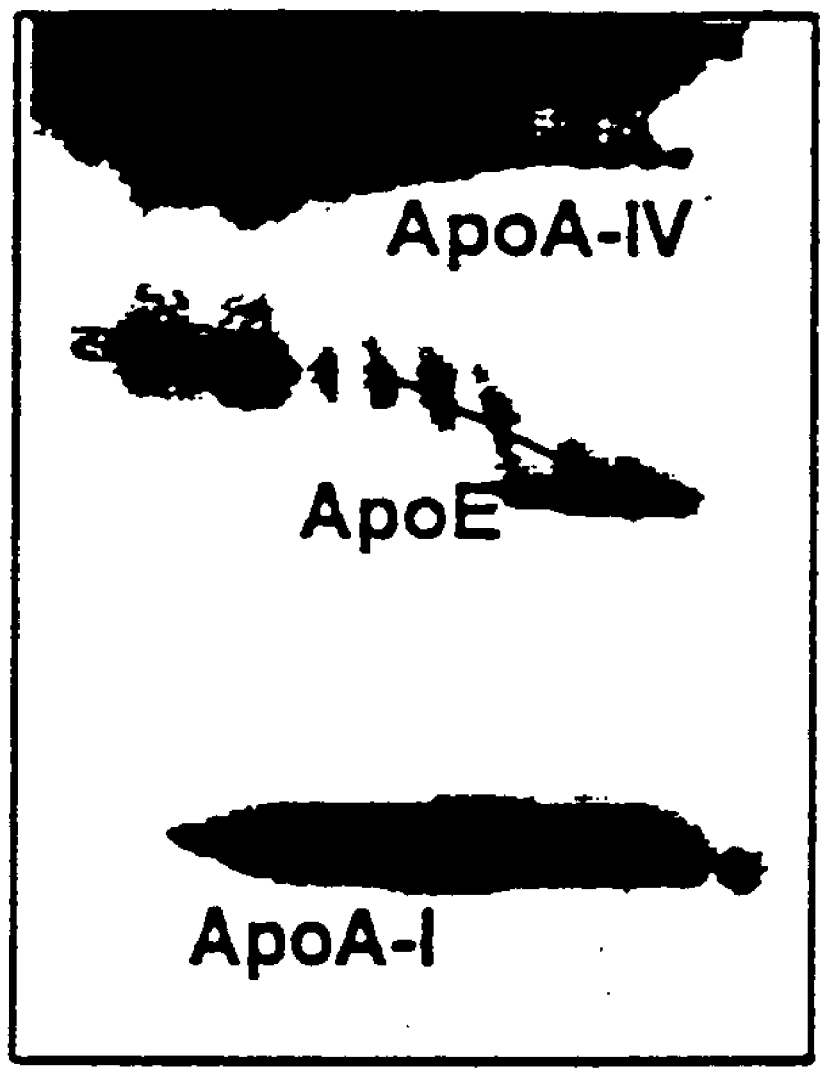

In order to show that other proteins do not completely displace the ApoE pre-adsorbed on the PBCA particles from the particle surface after an i.v. application, the particles with pre-adsorbed ApoE (cf. Example 2) were incubated according to the standard procedure for the 2-DE in plasma (5 min at 37° C., according to Blunk, see Example 2) and the resulting adsorption patterns determined. FIG. 2 shows sections from the 2-DE-gel which contain the ApoE spots.

Example 4

Figure 3:
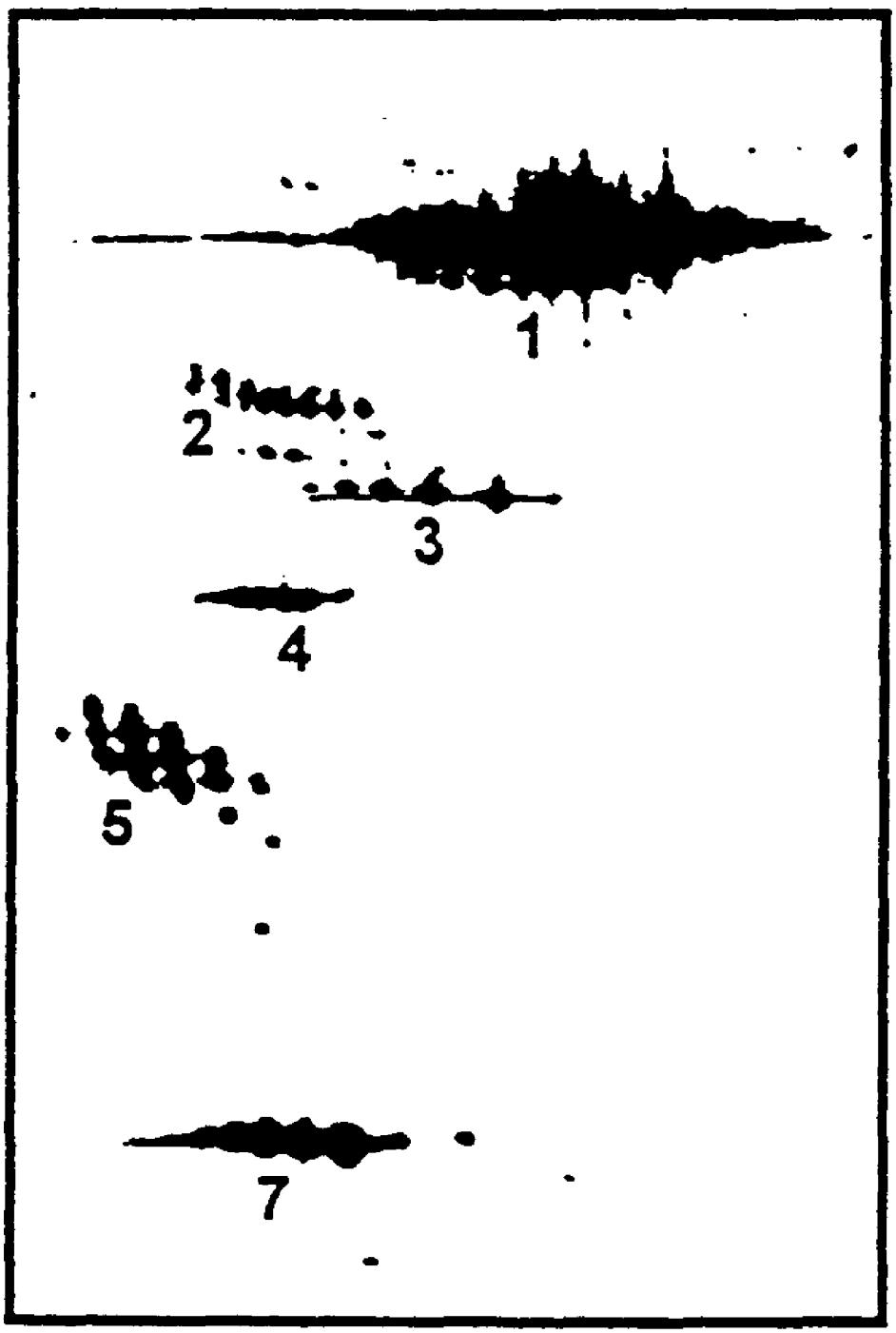
Figure 4:
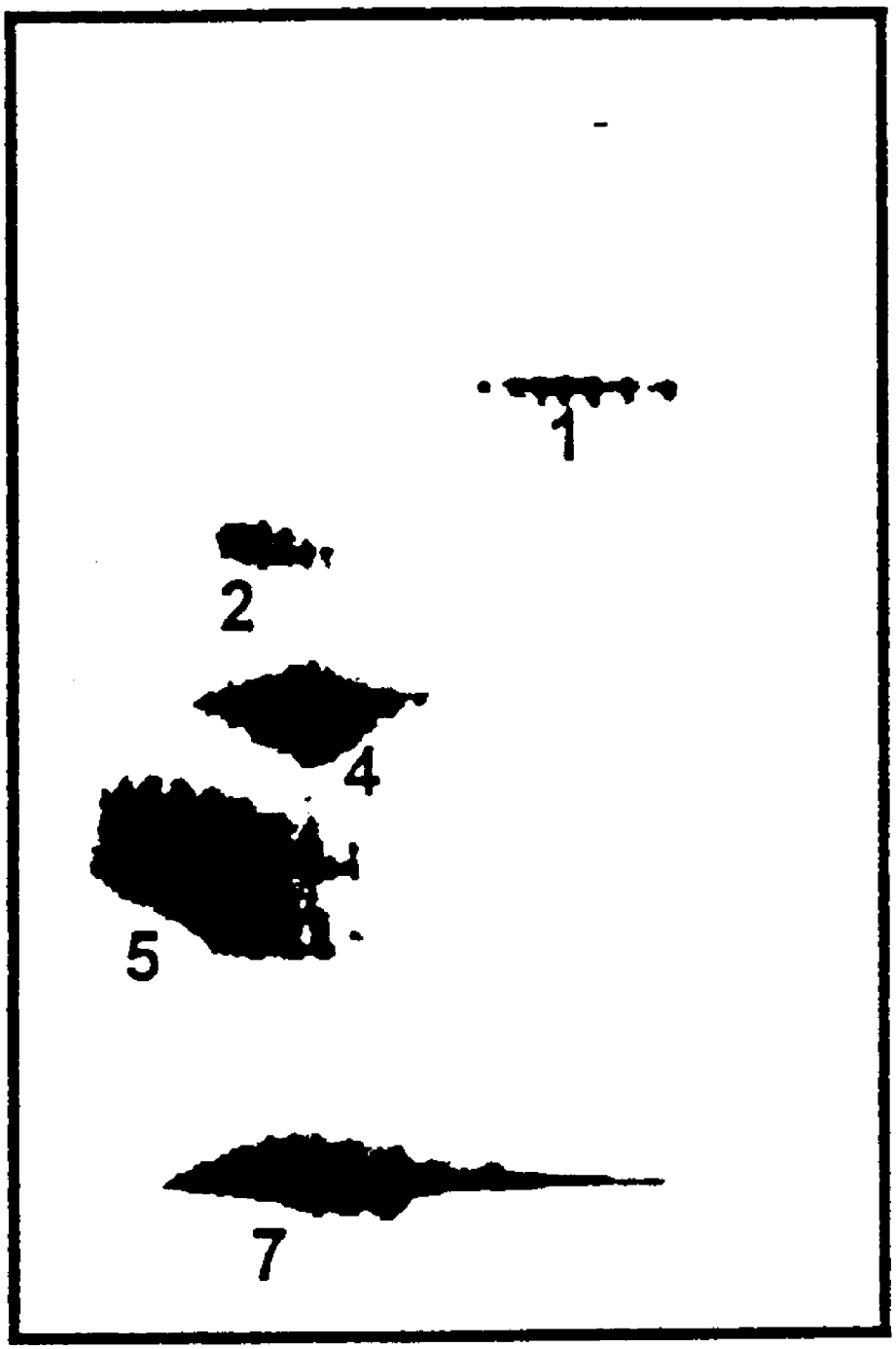

The plasma protein adsorption patterns of PBCA particles which mediated no analgesic effect of dalargin in the CNS were determined. FIG. 3 shows the gel obtained with unmodified PBCA particles. No ApoE was detected. FIG. 4 shows the gel obtained with PBCA particles modified with poloxamer 407. Again, no ApoE was detected and it was thus shown that no CNS effectiveness results in the absence of ApoE.

Example 5

Chemical coupling of apolipoprotein E to carboxylated polymethyl methacrylate nanoparticles:

A polymethyl methacrylate latex (particle diameter 65 nm±10%) functionalized with carboxyl groups on the surface is made up to 0.5% after two wash steps (30,000 rpm/10 min, 4° C.) with 0.01M phosphate buffer solution, pH 6.5. At 4° C. 0.5 ml of the latex are reacted with 300 μl of protein solution and incubated for 60 min. 10 mg of water-soluble carbodiimide(1-ethyl-3-(3-dimethylaminopropyl)-carbodiimide hydrochloride) are now added. The mixture is shaken overnight (16 hrs) on a low-frequency agitator. The particles are separated from the medium by centrifugation (30,000 rpm/10 min, 4° C.) and redispersed in 0.1M glycine buffer, pH 8.55, to give a solids content of 0.5%

Example 6

Chemical coupling of apolipoprotein E to polymethyl methacrylate latex surface-functionalized by introduction of epoxy groups:

A core-shell latex (core: polymethyl methacrylate; shell: polyglycidylmethacrylate) with a particle diameter of 70 nm±10% is made up to 2% solids content after two wash steps (30,000 rpm/10 min, 4° C.) with 0.0025M phosphate buffer, pH 8.0. Equal volumes of the latex and a 0.2% protein solution are shaken on a agitator for 3 hours at 28° C. Subsequently, centrifugation is carried out (30,000 rpm/ 10 min, 4° C.) and the sediment redispersed in GBS buffer, pH 8.0, so that the latex has a solid content of 0.5%.

Table 1: CNS effectiveness of unmodified PBCA nanoparticles and PBCA nanoparticles surface-modified with various surfactants, charged with dalargin, after intravenous administration to mice (dalargin dose: 10 mg/kg). The analgesic effects given are expressed as a percentage of the maximum possible effect (% MPE) (S: standard deviation, n=4) (calculation formula according to Alyautdin, R. N., Gothier, D., Petrov, V. E., Kharkevich, D. A., Kreuter, J., *Eur. J. Pharm. Biophar.*, 41, 44–48, 1995)

| surface-modifying surfactant | % of MPE (after 15 min) | S | % of MPE (after 45 min) | S |
|---|---|---|---|---|
| Tween 20 | 79.7 | ±21.3 | 52.9 | ±20.9 |
| Tween 40 | 87.5 | ±16.1 | 60.8 | ±38.0 |
| Tween 60 | −7.1 | ±24.2 | 45.5 | ±36.6 |
| Tween 80 | 100 | ±0 | 10.5 | ±14.9 |
| Poloxamer 407 | 4.4 | ±3.9 | 9.5 | ±5.8 |
| Poloxamer 908 | −1.3 | ±3.6 | 4.2 | ±5.5 |
| Poloxamer 188 | 8.1 | ±5.9 | 3.3 | ±3.4 |
| Poloxamer 184 | 0.9 | ±0.28 | 1.0 | ±2.3 |
| Poloxamer 338 | 0.2 | ±0.5 | 1.4 | ±3.9 |
| Cremophor EL | 10.9 | ±13.1 | 8.6 | ±8.7 |
| unmodified particles | 2.3 | ±1.6 | 3.7 | ±11.7 |

Dalargin dose: 7.5 mg/kg

Diagram 1: Sections with ApoE spots from 2-DE gels of unmodified PBCA particles (left) and PBCA particles surface-modified with Tween 80 (right) each after pre-adsorption of ApoE. The unmodified particles also had a CNS effectiveness due to the adsorbed ApoE (Example 2).

Diagram 2: Section from the 2-DE gel of unmodified PBCA particles with pre-adsorbed ApoE after incubation in plasma (Example 3). Abscissa: non-linear gradient pI 4.5–6.0 Ordinate: non-linear gradient MW 25,000–46,000

Diagram 3: 2-DE gel of unmodified PBCA particles without CNS effectiveness (Example 4). (1) albumin, (2) αl-antitrypsin, (3) fibrinogen γ, (4) ApoA-IV, (5) ApoJ, (7) ApoA-I Abscissa: non-linear gradient pI 4.5–6.5 Ordinate: non-linear gradient MW 25,000–75,000

Diagram 4: 2-DE gel of PBCA particles surface-modified with poloxamer 407 without CNS effectiveness (Example 4) (1) Albumin, (2) αl-antitrypsin, (4) ApoA-IV, (5) ApoJ, (7) ApoA-I Abscissa: non-linear gradient pI 4.5–6.5 Ordinate: non-linear gradient MW 25,000–75,000

What is claimed is:

1. Drug carrier particles, in active substance-loaded or active substance-free form, comprising carrier particles having at least one recognition protein or at least a receptor-recognizing molecule part of a recognition protein covalently bound ex-vivo to reactive surface groups present on the carrier particles.

2. Drug carrier particles according to claim 1, wherein the particle material comprises polymers, the drug (nanosuspensions, hydrosols), solid lipids, liquid lipids, o/w emulsions, w/o/w emulsions or phospholipid vesicles.

3. Drug carrier particles according to claim 1, wherein the binding to the particles has been effected with epoxy or aldehyde groups, or after activation of the particle surface with activators.

4. Drug carrier particles according to claim 3, wherein the activator is selected from the group consisting of carbodiimide, n-ethoxycarbonyl-2-ethoxy-1,2-dihycroquinoline, glutardioldehyde, bromozyane, meta-periodate (Na-salt or K-salt), tosyl chloride and chloroformic acid ester.

5. Drug carrier particles according to claim 3, wherein the binding of the recognition proteins has been effected via amino groups.

6. Drug carrier particles according to claim 1, wherein the recognition protein is a recognition protein occurring naturally in blood.

7. Drug carrier particles according to claim 1, wherein the recognition protein is apolipoprotein E, A-I, A-II, A-IV, B, C-II, C-III, D, H and/or J.

8. Drug carrier particles according to claim 7, wherein the recognition protein apolipoprotein E is present in combination with one or more other recognition proteins.

9. Drug carrier particles according to claim 8, wherein the other recognition proteins are selected from the group consisting of apolipoprotein A-I, A-II, A-IV, B, C-II, C-III, D, H and J, and/or albumin.

10. Drug carrier particles according to claim 1, wherein apo C-II, apo C-III, apo-A-IV, apo-E are used individually or in combinations of 2, 3 or 4 apolipoprotein.

11. Drug carrier particles according to claim 1, wherein the recognition protein is present, in relation to the drug carrier, in an amount of 0.001 to 40 wt. %.

12. Drug carrier particles according to claim 1, wherein the recognition protein is present, in relation to the drug carrier, in an amount of 0.01 to 30 wt. %.

13. Drug carrier particles according to claim 1, wherein the recognition protein is present, in relation to the drug carrier, in an amount of 0.1 to 15 wt. %.

14. Drug carrier particles according to claim 1, wherein for increased circulation time in blood, which contain an amount of ApoE which is insufficient for an accumulation in a central nervous system or contain no ApoE in combination with one or more of the apolipoproteins A-I, A-II, A-IV, C-II, and C-III.

15. Drug carrier particles according to claim 1, wherein the particles are present in the form of solid or liquid particles, suspensions or emulsions of solid or liquid particles.

16. Drug carrier particles according to claim 15, wherein the particles are in the form of amorphous or crystalline nana- or microparticles, o/w emulsions, w/o/w emulsions or liposomes, or in the form of nanosuspensions or hydrosols.

17. Drug carrier particles, in active substance-loaded or active substance-free form, comprising carrier particles having at least one recognition protein or at least a receptor-recognizing molecule part of a recognition protein bound to a surface of the carrier particles ex-vivo by preferential adsorption, wherein the surface of the carrier particles having been chemically modified before the preferential adsorption by introducing functional groups or the surface properties changed by physical treatment with plasma.

18. Drug carrier particles according to claim 17, wherein the particle material comprises polymers, the drug (nanosuspensions, hydrosols), solid lipids, liquid lipids, o/w emulsions, w/o/w emulsions or phospholipid vesicles.

19. Drug carrier particles according to claim 18 wherein the binding to the particles has been effected with epoxy or aldehyde groups, or after activation of the particle surface with activators.

20. Drug carrier particles according to claim 19, wherein the activator is selected from the group consisting of carbodiimide, n-ethoxycarbonyl-2-ethoxy-1,2-dihycroquinoline, glutardioldehyde, bromozyane, metaperiodate (Na-salt or K-salt), tosyl chloride and chloroformic acid ester.

21. Drug carrier particles according to claim 18 wherein the binding of the recognition proteins has been effected via amino groups.

22. Drug carrier particles according to claim 18 wherein the surface was modified by the adsorption of substances which lead to a preferential adsorption of the recognition protein, the modifying substance being used in relation to the drug particle in a weight-related amount of 0.01 to 10 parts modifying substance per 1 part particle.

23. Drug carrier particles according to claim 18 wherein the surface was modified by the adsorption of substances which lead to a preferential adsorption of the recognition protein, the modifying substance being used in relation to the drug particle in a weight-related amount of 0.1 to 10 parts modifying substance per 1 part particle.

24. Drug carrier particles according to claim 18 wherein the surface was modified by the adsorption of substances which lead to a preferential adsorption of the recognition protein, the modifying substance being used in relation to the drug particle in a weight-related amount of 1 part modifying substance per 1 part particle.

25. Drug carrier particles according to claim 18, wherein the surface of the particles has been modified by the adsorption of a surfactant.

26. Drug carrier particles according to claim 25, wherein the surfactant is selected from the group consisting of ethoxylated surfactants.

27. Drug carrier particles according to claim 25, wherein the surfactant is selected from the group consisting of polyethylene glycol fatty acid esters and polyethylene glycol fatty alcohol esters.

28. Drug carrier particles according to claim 25, wherein the surfactant is selected from the group consisting of polyethylene glycol sorbitan fatty acid esters and polyethylene glycol fatty acid glycerides.

29. Drug carrier particles according to claim 25, wherein the surfactant is selected from the group consisting of Tween® 20, 40, 60 and 80, and Cremophor® E1 and RH40.

30. Drug carrier particles according to claim 18, wherein the surface of the particles has been modified by adsorption of a polymer.

31. Drug carrier particles according to claim 30, wherein the polymer is selected from the group consisting of poloxamers, polyxamines, celluloses, derivatives of celluloses.

32. Drug carrier particles according to claim 30, wherein the polymer is selected from the group consisting of methylcellulose, hydroxyethylcellulose, hydroxypropylmethylcellulose, hydroxypropylcellulose, carboxymethylcellulose sodium, xathan, polyvinyl alcohol, polyvinylpyrrolidone, polyacrylic acids, polyethyleneglycols, polyethyleneglycols-containing block copolymers, starch, starch derivatives, dextran, dextran derivatives, polyethyleneimine, and gelatins.

33. Drug carrier particles according to claim 18 wherein the recognition protein is a recognition protein occurring naturally in blood.

34. Drug carrier particles according to claim 18 wherein the recognition protein is apolipoprotein E, A-I, A-II, A-IV, B, C-II, C-III, D, H and/or J.

35. Drug carrier particles according to claim 18 wherein the recognition protein apolipoprotein E is present in combination with one or more other recognition proteins.

36. Drug carrier particles according to claim 35, wherein the other recognition proteins are selected from the group consisting of apolipoprotein A-I, A-II, A-IV, B, C-II, C-III, D, H and J, and/or albumin.

37. Drug carrier particles according to claim 18 wherein apo C-II, apo C-III, apo-A-IV, apo-E are used individually or in combinations of 2, 3 or 4 apolipoprotein.

38. Drug carrier particles according to claim 18 wherein the recognition protein is present, in relation to the drug carrier, in an amount of 0.001 to 40 wt. %.

39. Drug carrier particles according to claim 18 wherein the recognition protein is present, in relation to the drug carrier, in an amount of 0.01 to 30 wt. %.

40. Drug carrier particles according to claim 18 wherein the recognition protein is present, in relation to the drug carrier, in an amount of 0.1 to 15 wt. %.

41. Drug carrier particles according to claim 18 wherein for increased circulation time in blood, which contain an amount of ApoE which is insufficient for an accumulation in a central nervous system or contain no ApoE in combination with one or more of the apolioproteins A-I, A-II, A-IV, C-II, and C-III.

42. Drug carrier particles according to claim 18 wherein the particles are present in the form of solid or liquid particles, suspensions or emulsions of solid or liquid particles.

43. Drug carrier particles according to claim 42, wherein the particles are in the form of amorphous or crystalline nana- or microparticles, o/w emulsions, w/o/w emulsions or liposomes, or in the form of nanosuspensions or hydrosols.

44. A drug comprising:
at least one drug; and
carrier particles having at least one recognition protein or at least a receptor-recognizing molecule part of the recognition protein covalently bound ex-vivo to reactive surface groups present on the carrier particles.

45. A drug comprising:

at least one drug; and carrier particles having at least one recognition protein or at least a receptor-recognizing molecule part of a recognition protein bound to a surface of the carrier particles ex-vivo by preferential adsorption, and wherein the surface of the carrier particles having been chemically modified before the preferential adsorption by introducing functional groups or the properties changed by physical treatment with plasma.

46. A method of making a drug comprising:

combining at least one drug with carrier particles having at least one recognition protein or at least a receptor-recognizing molecule part of a recognition protein covalently bound ex-vivo to reactive surface groups on the carrier particles.

47. A method according to claim 46, wherein the drugs can be accumulated in the central nervous system.

48. A method according to claim 46, wherein the drug can be accumulated in tissues, at target locations or in cells.

49. A method according to claim 46, wherein the drug can be accumulated in bone marrow, liver, spleen, tumor tissues, tumor metastases, blood cells and nuclei.

50. A method of making a drug comprising:

combining at least one drug with carrier particles having at least one recognition protein or at least a receptor-recognizing molecule part of a recognition protein bound to the carrier particles ex-vivo by preferential adsorption, and wherein the surface of the carrier particles having been chemically modified before the preferential adsorption by introducing functional groups or the properties changed by physical treatment with plasma.

51. A method according to claim 50, wherein the drugs can be accumulated in the central nervous system.

52. A method according to claim 50, wherein the drug can be accumulated in tissues, at target locations or in cells.

53. A method according to claim 50, wherein the drug can be accumulated in bone marrow, liver, spleen, tumor tissues, tumor metastases, blood cells and nuclei.

54. A method for making drugs comprising at least one drug and carrier particles, the method comprising:

covalently bonding recognition proteins or receptor-recognizing molecule parts of recognition proteins to reactive surface groups of carrier particles ex-vivo.

55. A method for making drugs comprising at least one drug and carrier particles, the method comprising:

bonding recognition proteins or receptor-recognizing molecule parts of recognition proteins to carrier particles ex-vivo using preferential adsorption in which a surface of the carrier particles has been chemically modified before the preferential adsorption by introducing functional groups or properties changed by physical treatment with plasma.

* * * * *